(12) United States Patent
Osypka

(10) Patent No.: US 8,868,214 B2
(45) Date of Patent: *Oct. 21, 2014

(54) CARDIAC ELECTRODE ANCHORING SYSTEM

(75) Inventor: Peter Osypka, Rheinfelden-Herten (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 348 days.

This patent is subject to a terminal disclaimer.

(21) Appl. No.: 11/457,676

(22) Filed: Jul. 14, 2006

(65) Prior Publication Data

US 2006/0247752 A1 Nov. 2, 2006

Related U.S. Application Data

(62) Division of application No. 10/821,421, filed on Apr. 9, 2004.

(51) Int. Cl.
*A61N 1/05* (2006.01)
(52) U.S. Cl.
CPC .......... *A61N 1/059* (2013.01); *A61N 2001/0578* (2013.01)
USPC .......................................................... 607/126
(58) Field of Classification Search
USPC .......................................................... 607/126
See application file for complete search history.

(56) References Cited

U.S. PATENT DOCUMENTS

| 3,244,174 A | 4/1966 | Wesbey et al. |
|---|---|---|
| 3,474,791 A | 10/1969 | Bentov |
| 3,737,579 A | 6/1973 | Bolduc |
| 4,142,530 A | 3/1979 | Wittkampf |
| 4,161,952 A | 7/1979 | Kinney et al. |
| 4,258,724 A | 3/1981 | Balat et al. |
| 4,341,226 A | 7/1982 | Peters |

(Continued)

FOREIGN PATENT DOCUMENTS

| DE | 2219044 | 11/1972 |
|---|---|---|
| DE | 4425195 | 4/2003 |

(Continued)

OTHER PUBLICATIONS

Worley et al., Construction of a Multipolar Electrode System Referenced and Anchored to Endocardium for Study of Arrhythmias, American Physiological Society, 1986.*

(Continued)

*Primary Examiner* — Eric D. Bertram
(74) *Attorney, Agent, or Firm* — Faegre Baker Daniels LLP

(57) ABSTRACT

A cardiac electrode arrangement has one or several heart electrodes arranged on the exterior surface of a heart or attached to the heart from the outside and/or arranged with a pole in the cardiac tissue. The electrodes, which can be fixed in the operating position by an anchor, run to an implanted heart pacemaker. For positioning and affixing the anchor, a tool is used that is designed as a rod or stylet and acts on an attachment site of the anchor, whereby the anchor can be pushed into or through the myocardium. The anchor is, at the same time, attached to a tension element or thread, over which the electrode, which has an inner guide channel that accommodates the tension element or thread, can be moved in a fitted and controlled manner. In the operating position, the electrode can be connected to the tension element or thread located in the guide channel.

20 Claims, 7 Drawing Sheets

(56) References Cited

U.S. PATENT DOCUMENTS

| | | | |
|---|---|---|---|
| 4,355,642 A | 10/1982 | Alferness | |
| 4,378,023 A | 3/1983 | Trabucco | |
| 4,444,206 A | 4/1984 | Gold | |
| 4,444,207 A | 4/1984 | Robicsek | |
| 4,475,560 A | 10/1984 | Tarjan et al. | |
| 4,628,944 A | 12/1986 | MacGregor et al. | |
| 4,633,880 A | 1/1987 | Osypka et al. | |
| 4,735,205 A | 4/1988 | Chachques et al. | |
| 4,827,940 A | 5/1989 | Mayer et al. | |
| 4,991,578 A | 2/1991 | Cohen | |
| 5,009,229 A | 4/1991 | Grandjean et al. | |
| 5,217,027 A | 6/1993 | Hermens | |
| 5,241,957 A | 9/1993 | Camps et al. | |
| 5,246,014 A | 9/1993 | Williams | |
| 5,300,107 A | 4/1994 | Stokes et al. | |
| 5,314,462 A | 5/1994 | Heil et al. | |
| 5,314,463 A | 5/1994 | Camps et al. | |
| 5,318,543 A | 6/1994 | Ross et al. | |
| 5,327,909 A | 7/1994 | Kiser et al. | |
| 5,336,252 A | 8/1994 | Cohen | |
| 5,350,419 A | 9/1994 | Bendel et al. | |
| 5,385,579 A | 1/1995 | Helland | |
| 5,423,876 A | 6/1995 | Camps et al. | |
| 5,476,500 A | 12/1995 | Fain et al. | |
| 5,492,119 A | 2/1996 | Abrams | |
| 5,693,081 A | 12/1997 | Fain et al. | |
| 5,716,392 A | 2/1998 | Bourgeois et al. | |
| 5,755,767 A | 5/1998 | Doan et al. | |
| 5,807,399 A | 9/1998 | Laske et al. | |
| 5,836,994 A | 11/1998 | Bourgeois | |
| 5,871,532 A | 2/1999 | Schroeppel | |
| 6,041,258 A | 3/2000 | Cigaina et al. | |
| 6,173,206 B1 | 1/2001 | Shchervinsky | |
| 6,304,786 B1 | 10/2001 | Heil, Jr. et al. | |
| 6,360,129 B1 | 3/2002 | Ley et al. | |
| 6,360,130 B1 | 3/2002 | Van Venrooij et al. | |
| 6,370,434 B1 | 4/2002 | Zhang et al. | |
| 6,405,091 B1 | 6/2002 | Vachon et al. | |
| 6,434,431 B1 | 8/2002 | Camps et al. | |
| 6,459,937 B1 | 10/2002 | Morgan et al. | |
| 6,473,654 B1 | 10/2002 | Chinn | |
| 6,491,707 B2 | 12/2002 | Makower et al. | |
| 6,510,332 B1 | 1/2003 | Greenstein | |
| 6,512,958 B1 | 1/2003 | Swoyer et al. | |
| 6,535,764 B2 | 3/2003 | Imran et al. | |
| 6,567,704 B2 | 5/2003 | Sundquist et al. | |
| 6,613,062 B1 | 9/2003 | Leckrone et al. | |
| 6,626,919 B1 | 9/2003 | Swanstrom | |
| 6,671,553 B1 | 12/2003 | Helland et al. | |
| 6,671,561 B1 | 12/2003 | Moaddeb | |
| 6,673,058 B2 | 1/2004 | Snow | |
| 6,752,813 B2 | 6/2004 | Goldfarb et al. | |
| 6,842,648 B2 | 1/2005 | Partridge et al. | |
| 6,934,589 B2 | 8/2005 | Sundquist et al. | |
| 6,941,174 B2 | 9/2005 | Shchervinsky | |
| 6,961,621 B2 | 11/2005 | Krishnan et al. | |
| 7,418,298 B2 * | 8/2008 | Shiroff et al. | 607/126 |
| 7,499,757 B2 | 3/2009 | Coe et al. | |
| 2001/0000349 A1 | 4/2001 | Coe et al. | |
| 2001/0039436 A1 | 11/2001 | Frazier et al. | |
| 2002/0013571 A1 | 1/2002 | Goldfarb et al. | |
| 2002/0072787 A1 | 6/2002 | Partridge | |
| 2002/0077685 A1 | 6/2002 | Sundquist et al. | |
| 2002/0123785 A1 | 9/2002 | Zhang | |
| 2002/0165589 A1 | 11/2002 | Imran et al. | |
| 2002/0183818 A1 | 12/2002 | Williams et al. | |
| 2003/0023295 A1 | 1/2003 | Osypka | |
| 2003/0028232 A1 | 2/2003 | Camps et al. | |
| 2003/0045919 A1 | 3/2003 | Swoyer et al. | |
| 2003/0055463 A1 | 3/2003 | Gordon et al. | |
| 2003/0125787 A1 | 7/2003 | Shchervinsky | |
| 2003/0204231 A1 | 10/2003 | Hine et al. | |
| 2004/0010282 A1 | 1/2004 | Kusleika | |
| 2004/0015193 A1 | 1/2004 | Lamson et al. | |
| 2004/0054388 A1 | 3/2004 | Osypka | |
| 2004/0260371 A1 | 12/2004 | Greenland et al. | |
| 2005/0033394 A1 | 2/2005 | Seifert et al. | |
| 2005/0033395 A1 | 2/2005 | Seifert et al. | |
| 2005/0033396 A1 | 2/2005 | Osypka | |
| 2005/0070986 A1 | 3/2005 | Tockman et al. | |
| 2005/0113900 A1 | 5/2005 | Shiroff et al. | |
| 2005/0113901 A1 | 5/2005 | Coe et al. | |
| 2005/0137672 A1 | 6/2005 | Coe et al. | |
| 2008/0249596 A1 | 10/2008 | Shiroff et al. | |

FOREIGN PATENT DOCUMENTS

| | | |
|---|---|---|
| EP | 1000634 | 5/2000 |
| EP | 1000634 A | 5/2000 |
| EP | 1025802 | 8/2000 |
| EP | 1025802 A1 | 8/2000 |
| GB | 2025236 | 1/1980 |
| GB | 2025236 A | 1/1980 |
| WO | 2004091716 | 10/2004 |
| WO | 2005028023 | 3/2005 |

OTHER PUBLICATIONS

Office Action received in related case U.S. Appl. No. 10/971,577, mailed Aug. 7, 2007.

Office Action received in related case U.S. Appl. No. 10/971,549, mailed Jul. 27, 2007.

Office Action recieved in related case U.S. Appl. No. 10/972,049, mailed Jul. 2, 2007.

German Office Action citing prior art to related German Patent Application and English translation thereof.

Epstein et al, Long-Term Performance of Bipolar Epicardial Atrial Pacing Using an Active Fixation Bipolar Endocardial Lead, PACE, Apr. 1998.

Office Action received in related case U.S. Appl. No. 10/972,298, mailed Apr. 17, 2007.

Office Action received in related case U.S. Appl. No. 10/972,049, mailed Jul. 24, 2006.

Office Action received in related case U.S. Appl. No. 10/972,049, mailed Jan. 11, 2007.

Office Action received in related case U.S. Appl. No. 10/971,549, mailed Feb. 2, 2007.

Office Action received in related case U.S. Appl. No. 10/821,421, mailed May 25, 2006.

Office Action received in related case U.S. Appl. No. 10/821,421, mailed Nov. 24, 2006.

Office Action received in related case U.S. Appl. No. 10/821,421, mailed Mar. 22, 2007.

International Search Report and Written Opinion of International Application No. PCT/US2004/010907, filed Apr. 9, 2004, both mailed Sep. 16, 2004.

International Search Report and Written Opinion of International Application No. PCT/US2004/035172, filed Oct. 22, 2004, both mailed Jan. 31, 2005.

Agreement between Cardiac Pacemakers, Inc. and Dr. Osypka GmbH, Aug. 26, 2002.

European Search Report issued in EP 10075223, dated Jul. 28, 2010.

German Office Action citing prior art to related German Patent Application and English translation thereof. Dec. 1, 2006.

Assad et al., New Lead for In-Utero Pacing for Fetal Congenital Heart Block, Journal of Thoracic and Cardiovascular Surgery, Jul. 2003.

Epstein et al., Long-Term Performance of Bipolar Epicardial Atrial Pacing Using an Active Fixation Bipolar Endocardial Lead, PACE, Apr. 1998.

Karpawich et al., Improved Epimyocardial Pacing, PACE, Nov. 1994.

Worley et al., Construction of a Multipolar Electrode System Referenced and Anchored to Endocardium for Study of Arrhythmias, American Physiological Society, 1886.

* cited by examiner

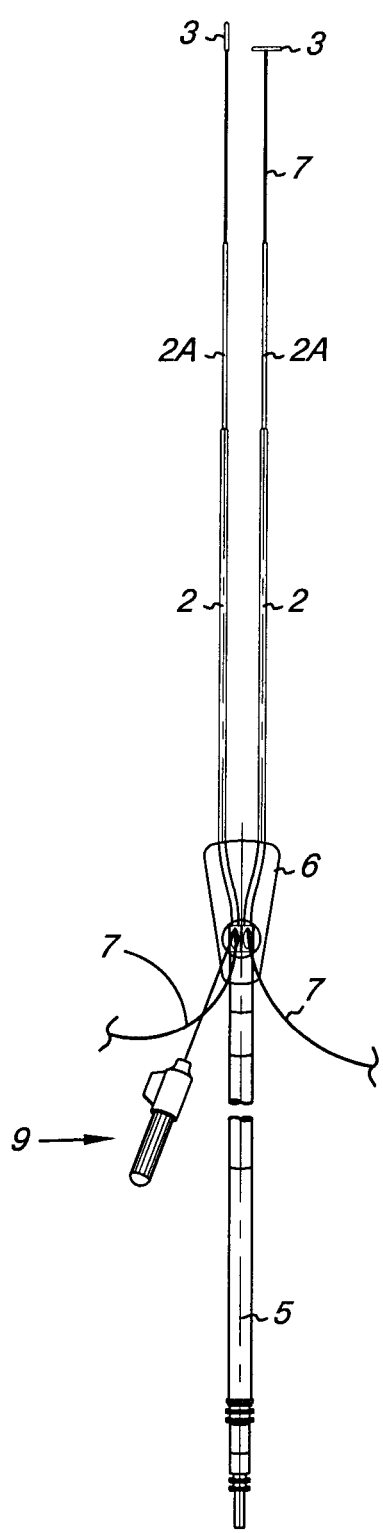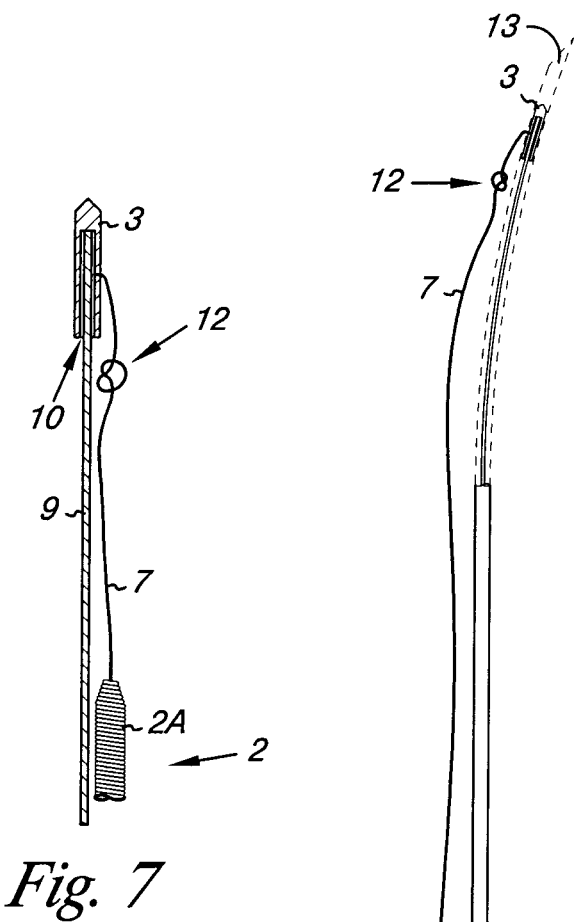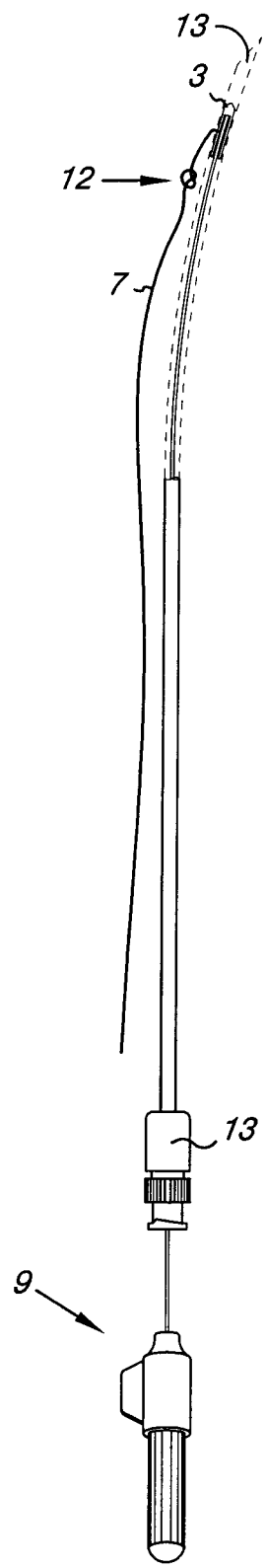
Fig. 6
Fig. 7
Fig. 8

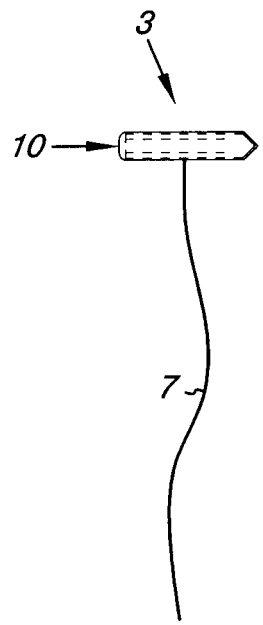 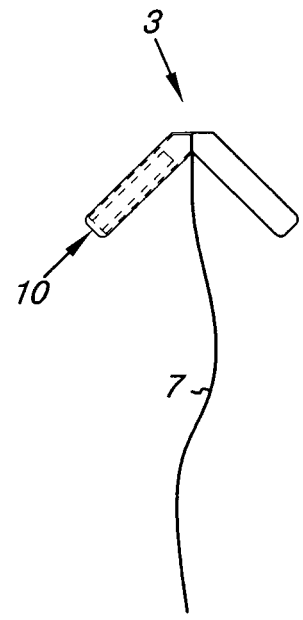 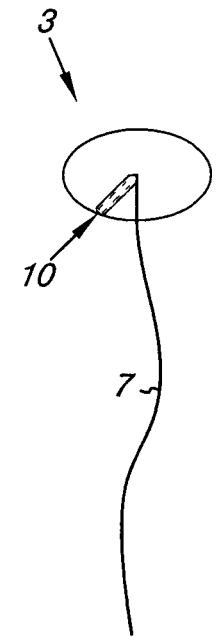 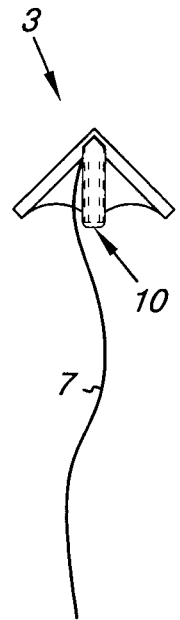
Fig. 11  Fig. 12  Fig. 13  Fig. 14
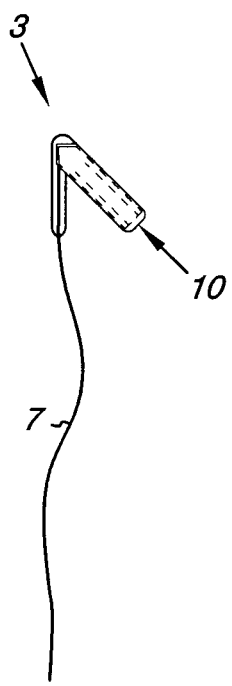 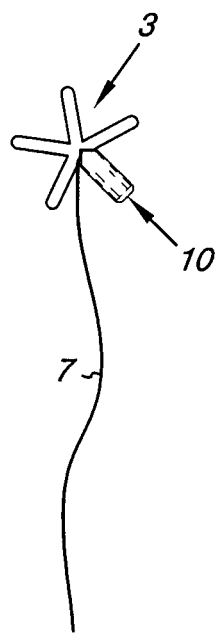 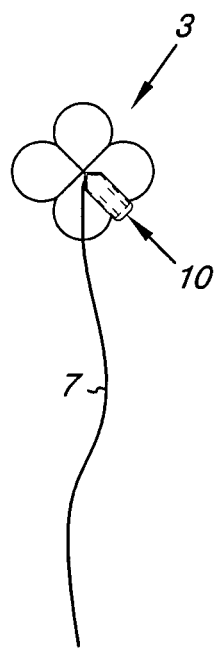
Fig. 15  Fig. 16  Fig. 17

CARDIAC ELECTRODE ANCHORING SYSTEM

RELATED APPLICATIONS

This application is a divisional of U.S. patent application Ser. No. 10/821,421 titled CARDIAC ELECTRODE ANCHORING SYSTEM filed on Apr. 9, 2004, which claims the benefit of German Patent Application No. 103 16 177.5-54, titled CARDIAC ELECTRODE ANCHORING SYSTEM filed on Apr. 10, 2003, the entire disclosures of which are hereby incorporated herein by reference.

TECHNICAL FIELD

This invention relates to a heart pacemaker electrode arrangement having an electrode that acts upon the outside of a heart and/or is arranged with a pole in the heart tissue, and runs to an implanted heart pacemaker. The electrode can be fixed in the operating position by an anchor. This invention further includes a tool that serves the positioning and fixing of the anchor.

BACKGROUND

The use of pacemaker electrodes for myocardial stimulation of the heart are known from DE 2 219 044.9 and U.S. Pat. No. 4,355,642. Serving there as anchors are epicardial screw electrodes, which must be screwed into a fatless area of the exterior of the heart in order to attain a sufficient stimulus threshold. Moreover, such electrodes require visual contact with the heart during the implantation. The necessary size of these electrodes and their anchoring means can lead to considerable problems, primarily in the case of juvenile hearts. If a biventricular stimulation of the heart is required, these relatively large anchors of the individual electrodes must be situated on both the left and the right ventricles.

There is a need therefore for an electrode arrangement of the type specified, whereby the opening of the rib cage is hardly required, since minimally-invasive access to the heart is enabled, and yet the electrode can be securely fixed in the myocardium without requiring consideration of the outer fat layer. At the same time, the space required for applying the electrode to the exterior heart surface should be kept to a minimum.

SUMMARY

In one embodiment, the present invention is a method for inserting an electrode within a myocardium of a heart. An anchor coupled to a tension element is inserted through the myocardium to an operating position adjacent an exterior surface of the myocardium. An electrode defining an inner guide channel for accommodating the tension element and having a pole at an end for stimulating the myocardium is provided. The electrode is advanced into the myocardium over the tension element. The tension element is affixed to the electrode at a connection point to prevent movement of the electrode in a direction away from the anchor.

In another embodiment, the present invention is a method for inserting an electrode within a myocardium of a heart. An anchor coupled to a tension element is inserted through the myocardium to an operating position adjacent an exterior surface of the myocardium. The anchor is manipulated into an abutment configuration relative to the exterior surface of the myocardium. An electrode having a pole for stimulating the myocardium is advanced over the tension element. The tension element is affixed to the electrode.

In yet another embodiment, the present invention is a method for inserting an electrode within a myocardium of a heart. An anchor coupled to a tension element is inserted through the myocardium to an operating position adjacent an exterior surface of the myocardium. The anchor is manipulated to an abutment configuration relative to the exterior surface of the myocardium. An electrode having a pole at an end is advanced over the tension element. The tension element is affixed to the electrode at a connection point to prevent movement of the electrode in a direction away from the anchor.

BRIEF DESCRIPTION OF THE DRAWINGS

FIG. 6 shows a view of the double electrode with the stylet, which is pushed into the left electrode and holds the anchor in the insertion location, and in comparison to this, an anchor in the swivelled-out operating position, represented at the end of the right electrode.

FIG. 7 shows a detailed representation of the region, indicated by a circle in FIG. 6, of the anchor held by the stylet and the tension element fastened to the anchor.

FIG. 8 shows a partially-sectioned view of an individual receiver tube or cannula with the pushed-in stylet, at the end of which the anchor is held, as well as the tension element running along the outside of the receiver tube or cannula.

FIGS. 11-17 show different embodiment forms of the anchor at the end of the tension element, with an attachment site for the tool indicated by a dashed line.

DETAILED DESCRIPTION

Figure 1:
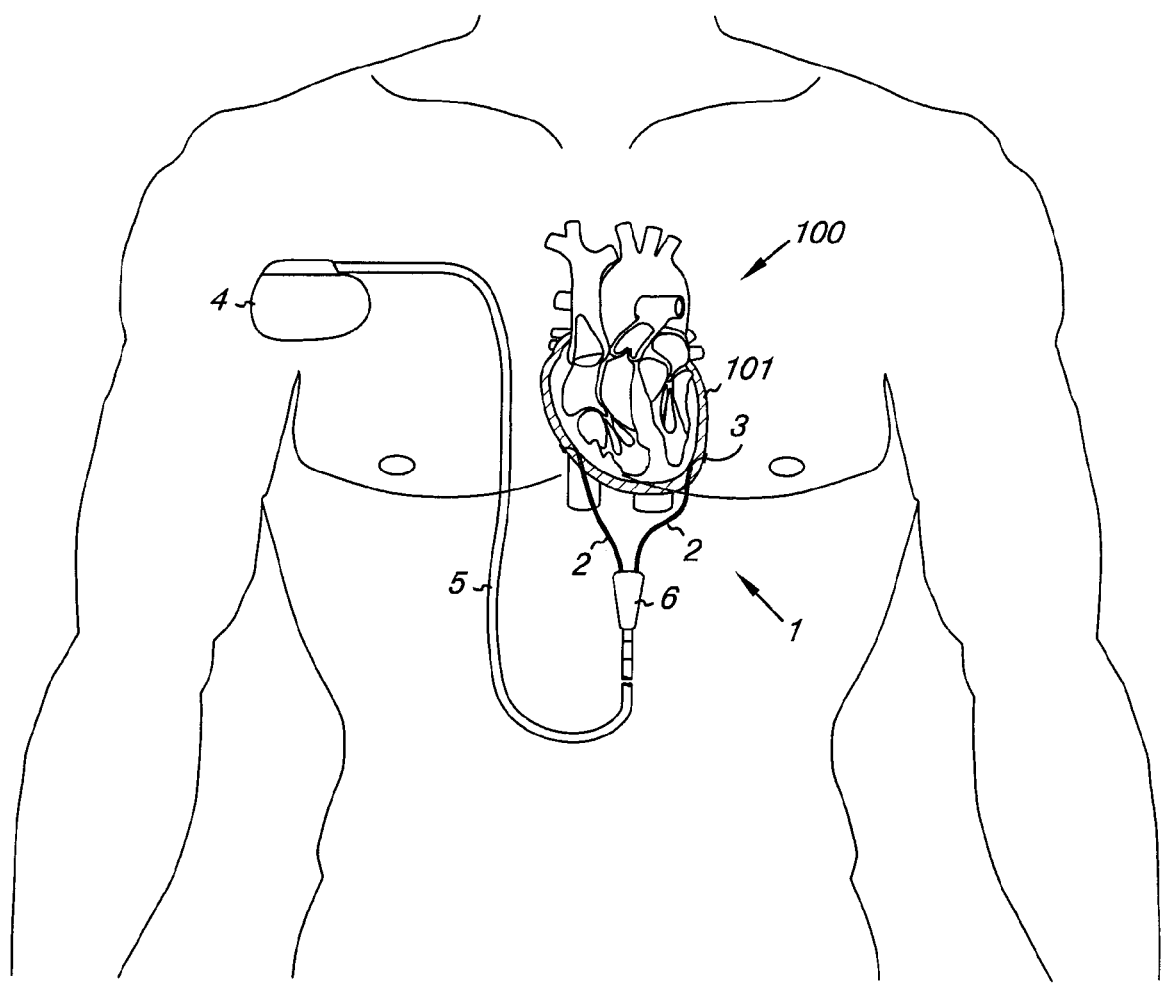
FIG. 1 shows an overall view of an electrode arrangement according to the invention, the arrangement having two electrodes branching out from a common supply lead at a connection point.

This invention proposes that a rod or stylet be provided as a tool, that an anchor have an attachment area for the tool, by which the anchor can be pushed into or through the myocardium, that the anchor be attached to a tension element or thread, via which the heart pacemaker electrode, which displays an inner guide channel and accommodates therein the tension element or the thread, can be moved in a fitted and controlled manner, and that the heart pacemaker electrode, in the use location, be connected or connectable to the tension element or thread situated in the guide channel of the electrode.

By these means, it is possible, without expensive rotary coils and without turning movement, to anchor the electrodes securely on the heart, if necessary under a fat layer, by first fixing the anchor and then guiding the electrode to the heart. The attachment of the electrode to the heart nevertheless takes place via this anchor, since the latter is fixed to the electrode with the aid of its tension element or thread. During the introduction of the electrode, the optimal stimulus threshold inside the myocardium can be simultaneously determined through an exterior measurement on the electrode. The required body opening can be small, since the anchor and the tension element fasted to the latter, as well as the electrode guided thereon are relatively small in cross section and thus can be introduced into and guided through a relatively small opening.

In this context, it is especially advantageous if the anchor has as the attachment site for the tool a deformation that can be detachably coupled to the tool. By this means, the anchor can be brought near to its operating position in a guided manner and placed in this position or its final operating position can be well controlled. If the anchor is in its operating position, the tool can be withdrawn or removed from the attachment site.

The attachment site on the anchor can be appropriately designed such that the anchor has at its back side, in the insertion direction, a reduced cross-section for an attachable end of the tool and/or a receiving aperture, open at the back end and closed at the opposite end, for the rod-shaped tool or stylet that fits into this aperture, whereby the anchor can be moved into or through the myocardium. Such a plug connection between the anchor and the tool associated with the electrode arrangement can be produced and undone again without great effort, which facilitates the application of the anchor to the myocardium. The attachment site of the anchor, during the insertion of the anchor and before the operating position is reached, points towards the rear in the insertion direction, while in the operating position, after the removal of the tool, it can also point in a different direction.

For affixing the heart pacemaker electrode in the operating position, it is advantageous if the heart pacemaker electrode has, at a distance from its end and from the anchor, at least one exit opening from its guide channel for the tension element or the thread, and if in the operating position the tension element or the thread is connected, at or on the outside this opening, to the heart pacemaker electrode, for example fixed or knotted to a loop. The tension element or the thread can in this case exit far enough from the exit opening (since the heart pacemaker electrode is pushed far enough in the direction of the anchor) that a sufficient contact of the heart pacemaker with the myocardium, thus a good stimulation of the myocardium, can be achieved and then maintained through fixing or knotting in this operating position.

The fixing or knotting of the tension element or the thread to the heart pacemaker electrode can appropriately take place such that the tension element is made taut between the anchor and its connection point to the heart pacemaker electrode. The heart pacemaker electrode is thereby fixed at its front and rear ends in its operating position and thus cannot slip or be moved either forward in the direction of the anchor or in the opposite direction towards the tension element or thread, and can thus be held long-term at the desired site in the myocardium in spite of the dynamic stress produced by the heartbeat.

For simple implantation of the heart pacemaker electrode in the myocardium, it is advantageous if the electrode arrangement has a receiver tube or cannula that holds the anchor and the tool during the feeding and/or insertion into the exterior of the heart and if, at the same time, the tension element or thread runs along the outside of the receiver tube or cannula. The receiver tube or cannula here serves the guiding of the tool and the anchor to the heart and into or through the myocardium up to the operating position of the anchor and, during the feeding and/or insertion of the anchor by means of the tool, can create or precut or preform a canal in the myocardium, in which canal the tension element and the end of the heart pacemaker electrode displaying the pole can be taken up. The tension element or thread running along the outside of the receiver tube or cannula is here likewise inserted into this myocardium canal, so that the heart pacemaker electrode can later be introduced into the myocardial canal by the tension element or thread. After the anchor has reached its operating position, the receiver tube or cannula can be withdrawn again from the myocardial canal without an accompanying withdrawal of the anchor and its tension element or thread. Subsequently, the heart pacemaker electrode can be moved into its operating position via the fixed and anchored tension element.

For a long-term and stable fixing of the anchor to the myocardium or to the outer end of the myocardial canal, as the case may be, and at the same time an easy mobility of the anchor with the aid of the tool and of the receiver tube or cannula, it is advantageous if the anchor in the operating position is formed by one or several barb-like parts or elements or pins or wings that during the insertion are collapsed and/or swung against a spring force during the insertion into the receiver tube or cannula. After leaving or withdrawal of the receiver tube or cannula, the parts can be expanded and/or swung into a position at an angle to the tension element. By this means, the anchor, during the positioning and before reaching its operating position, can be small enough in cross-section that it fits into the receiver tube or cannula or through the myocardial canal, as the case may be. After leaving the myocardial canal or the receiver tube or cannula of the anchor or, as the case may be, in its operating position, the anchor can unfold or swing out automatically or through a slight pull on the tension element or thread and thus become effective as an abutment for the tension element or thread acting upon the anchor.

According to one embodiment of the anchor, it has a rod form and the deformation or opening serving the receiving of the end of the tool runs in the longitudinal direction of this anchor and is designed in particular as a pocket hole, and the tension element is arranged between both ends of this rod-shaped anchor, leaving at an angle to the orientation of the rod-shaped anchor. By this means, the rod-shaped, oblong anchor can be arranged, guided, and held inside the receiver tube or cannula in the longitudinal direction, so that the tool can engage the opening on one of the front sides of the anchor. In the operating position, the anchor can then, after the detachment of the tool from the opening, swing out diagonally to the insertion direction or diagonally to the myocardial canal, as the case may be, especially outside the myocardium, or be swung out through actuation of the tension element and the forces acting thereby on the anchor between its ends.

It is especially advantageous for the swiveling of the anchor after leaving the myocardial canal if the tension element is arranged approximately in the center between the two ends of the rod-shaped anchor or nearer to the front end in the insertion direction than to the end displaying the deformation for the tool. By activating the tension element, the anchor can be easily swiveled or turned counter to the longitudinal direction of the myocardial canal, in that through the tension element the front end of the anchor is pulled towards the back and in this manner swiveled, and during this swiveling can rest with its long side against the myocardium, in particular at the exit of the myocardial canal or of the passage channel of the receiver tube.

For the quick and easy positioning of the heart pacemaker electrode at a location having an especially favorable stimulus threshold within the myocardial canal, it is advantageous if a stop is provided at a distance from the anchor on the tension element or thread for the electrode movable on the latter. By means of this stop, the end of the electrode in the operating position can be positioned on the heart at a fixed distance from the anchor. A positioning of the pole of the electrode immediately at the anchor is thereby avoided, experience having shown that the stimulus threshold there is unfavorable. The electrode is thereby fixed within the myocardium between this front stop on the tension element or thread and the fixing or knotting of the tension element or thread at the rear or outer end of the electrode. The quick and simultaneously secure positioning of the electrode also promotes a short operating time and thus a low degree of strain on the patient.

A simple and easily produced configuration of the front stop on the tension element or thread can consist in a thickening or knot on the tension element or thread, the cross section of which thickening or knot exceeds, at least in a region, the inner cross section of the guide channel or a narrowed section of the guide channel in the electrode.

In an expanded embodiment of the invention, the electrode arrangement has a biventricular design and can display a common supply lead from which two electrodes branch out and then run separately to the heart. Each of these electrodes has a guide channel and an anchor for attachment to the outside of the heart. Here, the common supply lead can run from a control device for the electrodes as near as possible to the heart, so that the supply lead and the branched electrodes connected to the latter can be guided through the rib cage to the heart in the least complicated manner possible and can be arranged at the heart in the operating position so as to cause a low degree of disturbance as well as to save space. In this double electrode embodiment, the electrodes can each be anchored to a ventricle of the heart, or both can be anchored to different locations on the same ventricle.

It is especially advantageous in this context if an exit opening from the guide channel located in the interior of the electrodes is provided at the branching location for each of the tension elements connected to an anchor. By this means, both tension elements can be fixed closely next to each other, whereby the operation of this double electrode arrangement can be made easier and an easy simultaneous controlling of the fixing of both tension elements at the connection location made possible.

The fixing of both tension elements at the connection location of the electrodes can take place such that the tension elements out of the electrodes, which proceed from a common branching point, can be or are knotted together for the fixing. Though this means, the electrodes can also be fixed relative to each other, a combination of the knotting together or fixing of the tension elements among each other and/or to a loop or another fastening element at the connection location also being possible.

In an especially body-tolerable or biocompatible embodiment of the anchor and the tension element, the anchor and/or the thread can consist of non-conducting material or of plastic, for example of non-dissolving surgical stitching material. Such materials are inexpensive and have a high strength, so that they can withstand, on a long-term basis, the dynamic stresses produced by the heart.

To be able to keep the myocardial canal as small in cross-section as possible, it is especially advantageous if the anode of the electrode is arranged outside the heart at a distance from the cathode or, as the case may be, from the pole situated on or in the heart, or, in the case of a biventricular, branched electrode, if the anodes are arranged in the region of the common supply lead before the branching. By this means, the long-term stressing of the heart through the electrode arrangement can be reduced.

It is advantageous for the long-term, stable fixing of the electrodes at the heart if the exit opening or exit openings for the tension elements or threads are closed in the operating position by means of a medical adhesive. This adhesive can effect an additional fixing of the knot of the tension elements to the exit openings, so that the knots are better protected against loosening.

Figure 4:
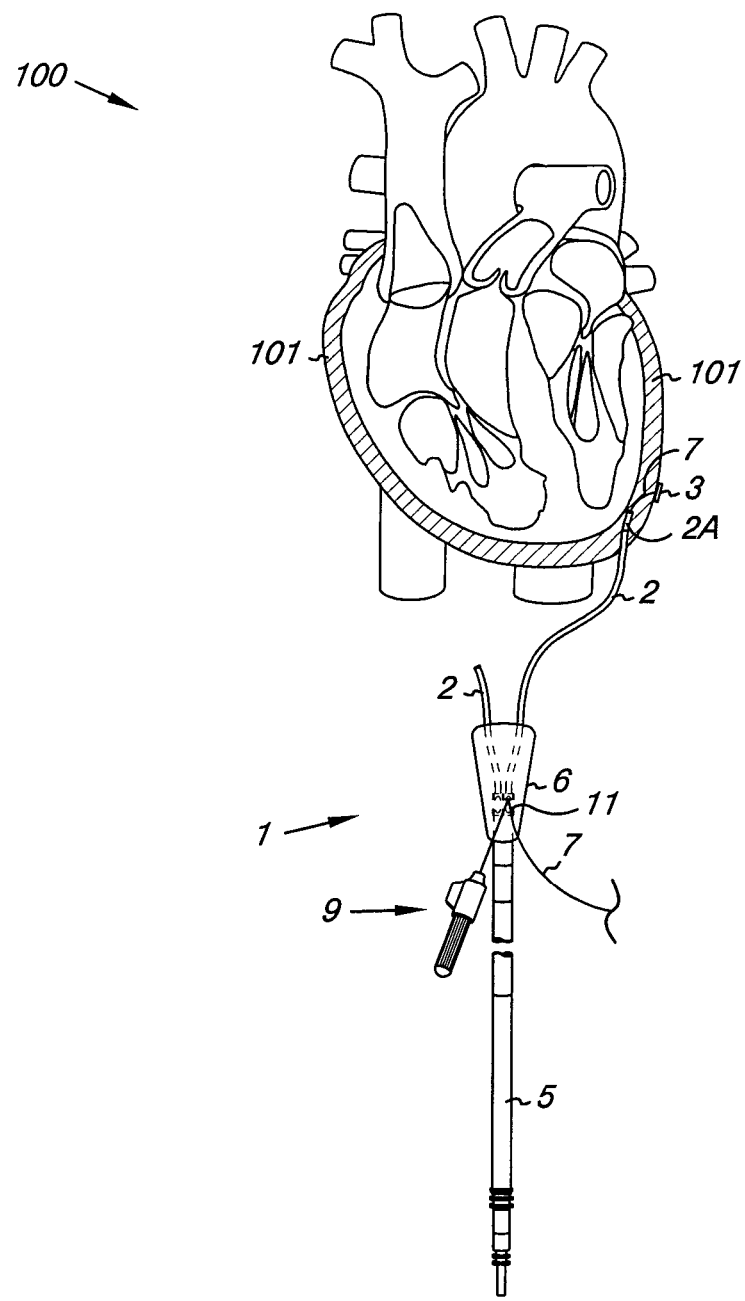
FIG. 4 shows an overall view of the electrode arrangement with a tool belonging to the arrangement and designed as a stylet for pushing in the anchor, viewed at the conclusion of the push-in process and shortly before the withdrawal of the tool.

FIG. 1 shows a heart pacemaker electrode arrangement 1 including a heart pacemaker electrode 2 with a pole 2a that can be fixed in the operating position in the cardiac muscle tissue (myocardium) 101 with the aid of an anchor 3 and is connected to an implanted heart pacemaker 4. FIGS. 1 and 4 show such an electrode arrangement 1 in which the electrode 2 has a biventricular design and displays a common supply lead 5 from the heart pacemaker 4 with two electrodes 2 that branch out at a branching location 6 and then run separately to the heart, each of which electrodes has an anchor 3. A tension element or thread 7 is fastened to the anchor 3 by means of which the heart pacemaker electrode 2, which includes an inner guide channel that receives therein the tension element or the thread 7, and which is guided in a movable and fitted manner.

Figure 10:
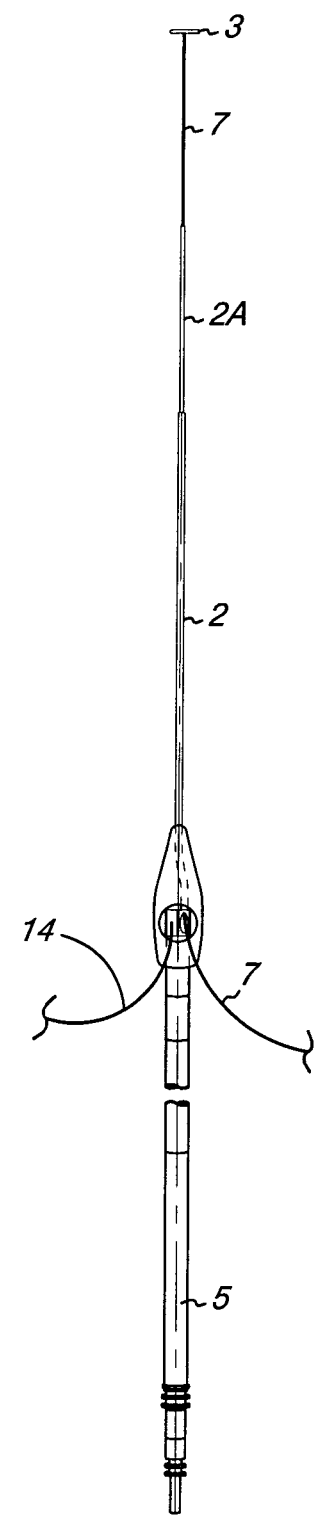

At a distance from its end and from the anchor 3, the electrode 2 has an exit opening 11 from its guide channel 8 for the tension element or thread 7, the tension element or thread 7 being fixed at or outside this opening by a knot or in some other manner. For this purpose, a loop or ring or similar fastening element (not shown) can be arranged near the exit opening 11. FIG. 10 shows an embodiment in which the tension element or thread 7 can be knotted to a thread 14 fastened near the exit opening 11. In addition, after the knotting, the exit opening 11 can be closed with a medical adhesive, to improve fixation of the knot.

Figure 5:
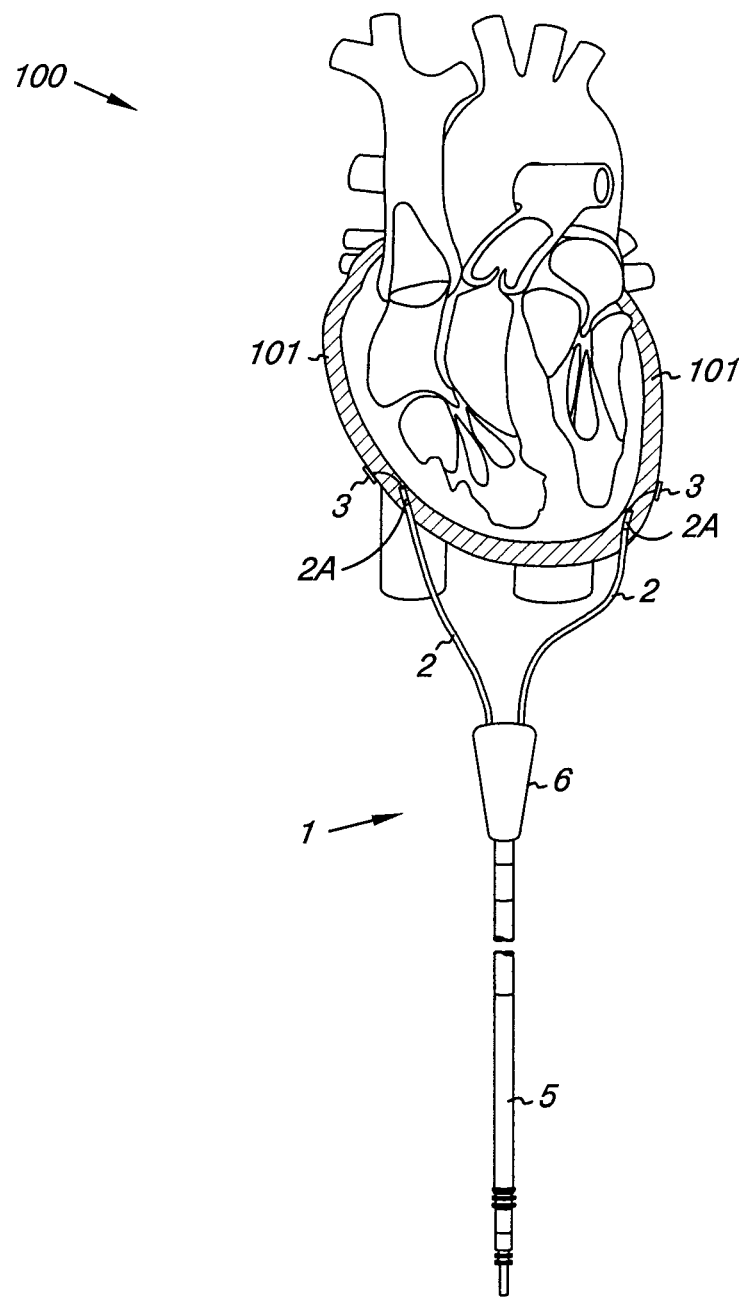
FIG. 5 shows an overall view, enlarged with respect to FIG. 1, of the electrode arrangement on the heart with a double electrode branching out from a branching location, the two anchors of both electrodes resting on the outside of the heart at the end of the passage channel that is opposite to the entrance into the myocardium.
Figure 9:
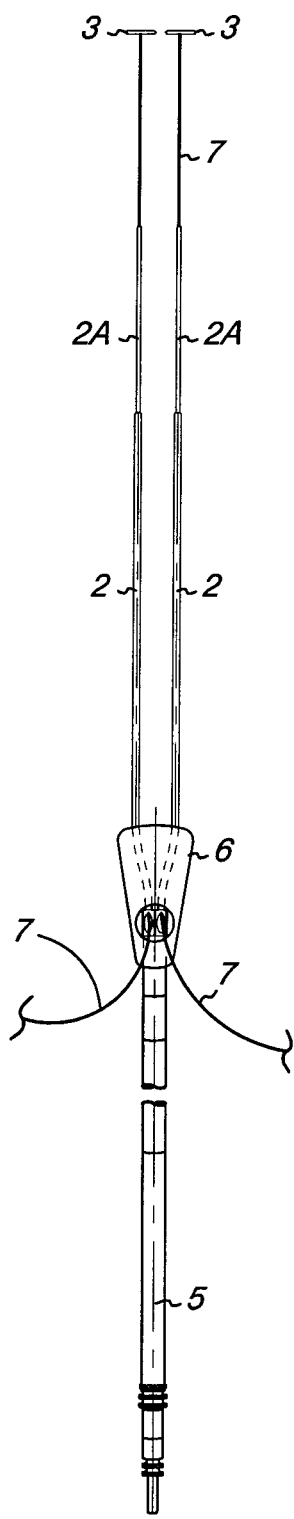
FIGS. 9 and 10 show a comparative representation of a double electrode and a single electrode with the tension element ending at the branching location or at the insertion location for the stylet.

To position and fix the anchor 3 on or in the myocardium 101, a tool is used, for which in one embodiment as shown in FIGS. 5, 6, and 8 is designed as a thin, flexible stylet 9. As the attachment site for the stylet 9, the anchor 3 has a receiving aperture 10 for the stylet 9 that fits into this opening, which is open at the rear end and closed at the opposite end, as is shown especially clearly in FIG. 7.

FIGS. 7 and 8 show that at a distance from the anchor 3 a stop 12 is provided on the tension element or thread 7 for the electrode 2 displaceable on the latter. Using this stop, the end of the electrode 2 can be positioned on the heart in the operating position at a fixed distance from the anchor 3. The stop 12 can, as shown here, consist of a simple knot on the tension element or thread 7 or some other thickening or projection or cross-sectional enlargement on the tension element or the thread 7, the cross-section of the stop 12 exceeding the inner cross section of the guide channel or a narrowed section of the guide channel in the electrode 2. Using this stop 12, which is impinged on by the front end of the electrode 2, and the knotting of the tension element or thread 7 at the exit opening 11 at the rear part of the electrode 2, the tension element or thread 7 is made taut between these two fastening points, thereby holding the electrode 2 guided thereon in its operating position.

Figure 2:
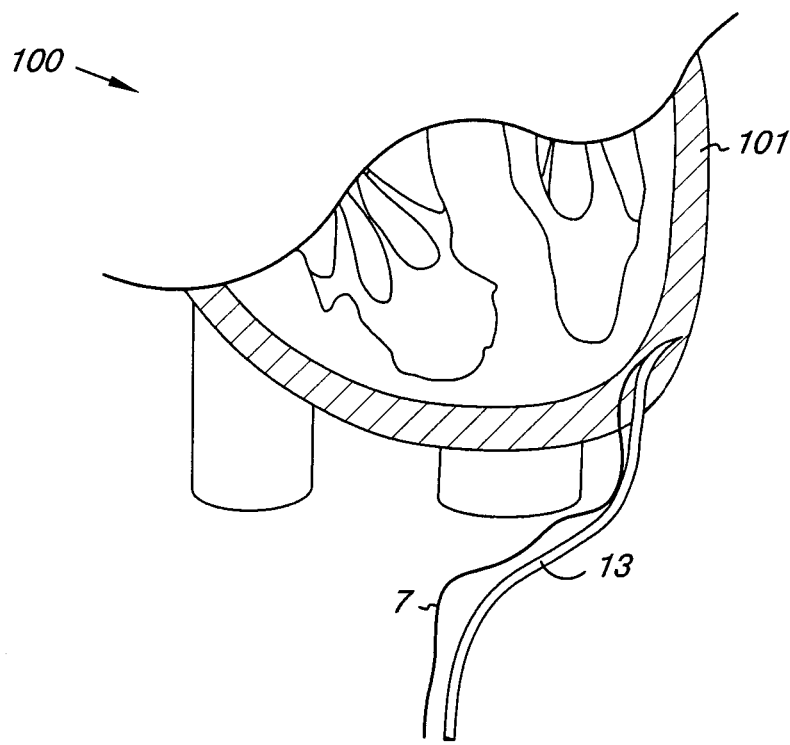
FIG. 2 shows a detailed view of a receiver tube or cannula belonging to the electrode arrangement, by means of which tube or cannula an anchor is guided from the outside of the heart into and through the myocardium, a tension element, which is attached to the anchor, running along the receiver tube or cannula at the outside.
Figure 3:
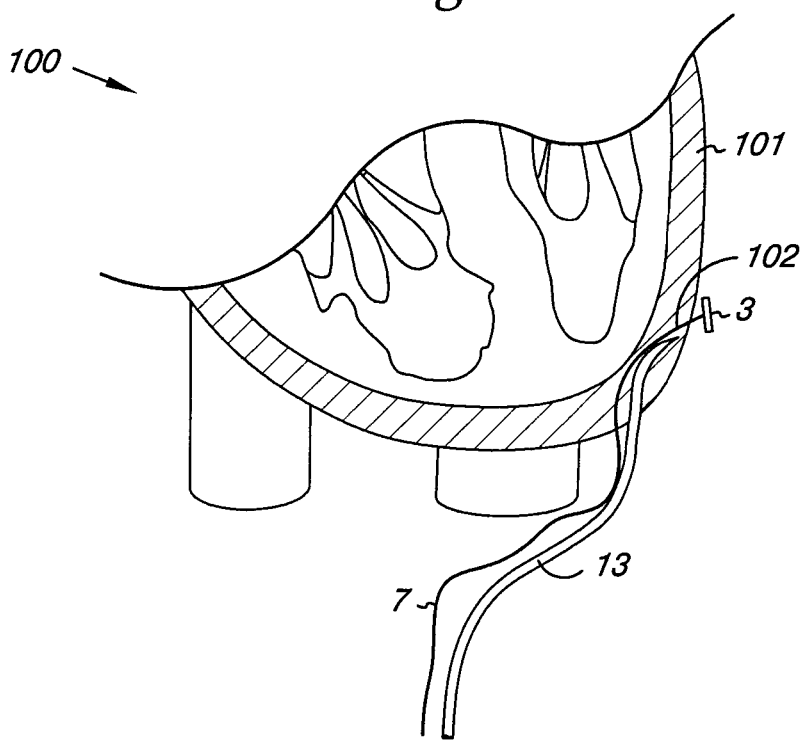
FIG. 3 shows a detailed view according to FIG. 2, in which the anchor, after having been moved through the myocardium, is located outside the myocardium in its unfolded state.

FIGS. 2, 3, and 8 also show that the anchor 3, along with the stylet 9 gripping it, is guided in a receiver tube or cannula 13. The tension element or thread 7 fastened to the anchor 3 here runs along the outside of the receiver tube or cannula 13. This receiver tube or cannula 13 punctures or pricks a canal 102 in or through the myocardium 101, through which channel the anchor 3 is pushed into its operating position at the outside of the heart. FIGS. 2 and 3 show this, and here the tension element or thread 7 running along the outside of the receiver tube or cannula 13 is shown in an exaggerated schematic representation. After the creation of the myocardial canal 102, the receiver tube or cannula 13 is withdrawn (FIG. 3) and the electrode 2 is pushed into the myocardial canal 102 via the tension element or thread 7 that runs through the myocardial canal 102 and is secured by the anchor 3, until the front end of the electrode 2 impinges on the stop 12 and comes to rest in the myocardium or, as shown in FIG. 5, with its pole 2a in the myocardium. Subsequently, the tension element or thread 7 is affixed to the exit opening 11 and thereby the electrode 2 is fastened at its back end to the tension element or thread 7.

When the anchor 3, guided by the stylet 9, leaves the myocardial canal 102 and is situated on the exterior surface of the heart, the stylet 9 is withdrawn from the receiving aperture 10 in the anchor 3. So that the anchor 3 may easily, advantageously, and automatically swing out into its operating position, the anchor 3 in the embodiment shown in FIGS. 1 through 10 has a rod-like shape, wherein the receiving aperture 10 runs in the longitudinal direction of the anchor 3 and having the form of a blind hole. The tension element or thread 7 is here arranged approximately at the center between both ends of the anchor 3, extending transverse with respect to the orientation of the anchor 3. The anchor 3 can thereby rest lightly against the exterior surface of the heart, transversely to the myocardial canal 102, and there anchor the tension element or thread 7.

In the embodiments shown in FIGS. 11 through 17, the anchor 3 displays variously-configured collapsible parts or elements or pins or wings, which are folded down against a spring force during insertion with the aid of the stylet 9 and the receiver tube or cannula 13 and which after leaving the receiver tube or cannula 13, or, as the case may be, the myocardial canal 102, spread out or unfold or swing out by virtue of the restoring force and assume a position transverse to the tension element or thread 7.

FIG. 11 once again shows the rod-shaped anchor 3 in its initial position before pivoting into a position along the receiver tube or cannula 13 and longitudinal to the tension element or thread 7. The pivoting or rotating of the anchor 3 occurs against a slight restoring force at the fastening site of the tension element or thread 7 on the longitudinal side of the anchor 3. FIG. 12, in contrast, shows an anchor 3 with two angled legs, one of the legs containing the receiving aperture 10. FIG. 13 shows an umbrella- or disk-shaped anchor 3 with a radially-oriented receiving aperture 10. FIG. 14 shows an anchor with three legs, wherein a membrane is stretched in each case between the central leg and one of the two outer legs. FIG. 15 shows a modification of the rod-shaped anchor 3 of FIG. 11, wherein the tension element or thread 7 is fastened to the front end of the anchor 3 via an angled reinforcement. FIG. 16 shows a star-shaped anchor 3 in which the receiving aperture 10 is provided in one of the legs of the star.

FIG. 17 shows a cloverleaf-shaped anchor 3 in which the receiving aperture 10 is arranged between two of the individual leaves.

In these embodiments, the receiving aperture 10 for the stylet 9 is oriented substantially rearwards on the anchor 3, to facilitate the insertion of the stylet 9 and to ensure that the tension element or thread 7 is likewise oriented during the insertion somewhat opposite to the insertion direction, to obstruct movement inside the myocardium as little as possible.

In the biventricularly designed electrode arrangement 1 shown in FIGS. 1, 4, 5, 6, and 9, for the purpose of biventricular stimulation of the heart, the two electrodes 2 run from the branching location 6 to the two ventricles on the heart, each being held in the myocardium with the aid of an anchor 3. In this case, provided at the branching location 6 is an exit opening 11 for each of the two tension elements or threads 7, where the two tension elements or threads 7 can be knotted together, thus fixing the two electrodes against each other and simultaneously at the branching location 6. A combination of the knotting of the tension elements or threads 7 to each other and to at least one of the loops of the exit opening 11 is also possible.

I claim:

1. A method for inserting an electrode within a myocardium of a heart, the method comprising:
    inserting an anchor coupled to a tension element through the myocardium to an operating position adjacent an outer surface of the heart;
    threading an electrode having an inner guide channel for accommodating the tension element and a pole for stimulating the heart over an end of the tension element;
    advancing the electrode over the tension element towards the inserted anchor until the pole contacts the heart; and
    affixing the tension element to the electrode at a connection point to prevent movement of the electrode in a direction away from the anchor.

2. The method of claim 1 comprising pre-forming a canal through the myocardium to the operating position adjacent the outer surface of the myocardium.

3. The method of claim 1 wherein inserting the anchor through the myocardium further comprises detachably coupling a tool to a deformation on the anchor.

4. The method of claim 1 further comprising manipulating the anchor to an orientation generally parallel to the outer surface of the myocardium in the operating position.

5. The method of claim wherein 1 affixing the tension element to the first electrode further comprises positioning a front end of the electrode against a stop on the tension element.

6. The method of claim 1 wherein affixing the tension element to the first electrode further includes knotting the tension element to a loop structure on the electrode.

7. The method of claim 1 wherein affixing the tension element to the electrode further comprises adhering the tension element to the electrode with a medical adhesive.

8. The method of claim 1 wherein affixing the tension element to the electrode further comprises tautly securing the tension element between the anchor and the connection point.

9. The method of claim 1 further comprising positioning a cathode of the electrode within the myocardium and an anode of the electrode at a distance from the cathode.

10. The method of claim 9 further comprising positioning the anode outside of the myocardium.

11. The method of claim 1 further comprising repeating the method to insert a second electrode within the myocardium, the second electrode branching out from a common supply lead with the first electrode.

12. The method of claim 11 further comprising fixing the tension elements extending through each of the first and second electrodes to each other.

13. The method of claim 1 wherein inserting the anchor to the operating position further comprises situating the anchor on the outer surface of the myocardium.

14. A method for inserting an electrode within a myocardium of a heart, the method comprising:
  inserting an anchor coupled to a tension element through the myocardium to an operating position adjacent an outer surface of the heart;
  manipulating the anchor into an abutment configuration relative to the outer surface of the heart;
  after inserting the anchor, advancing an electrode having a pole for stimulating the myocardium over the tension element towards the anchor; and
  coupling the tension element to the electrode.

15. The method of claim 14 wherein manipulating the anchor into the abutment configuration comprises maneuvering the anchor from a collapsed configuration to an expanded configuration.

16. The method of claim 14 wherein manipulating the anchor into the abutment configuration comprises swinging the anchor into an angled orientation relative to the tension element.

17. The method of claim 14 wherein manipulating the anchor into the abutment configuration comprises orienting the anchor diagonally relative to an insertion direction.

18. The method of claim 14 wherein manipulating the anchor into the abutment configuration comprises orienting the anchor generally parallel to the outer surface of the myocardium in the operating position.

19. The method of claim 14 wherein manipulating the anchor into the abutment configuration comprises pulling on the tension element.

20. A method for inserting an electrode within a myocardium of a heart, the method comprising:
  inserting an anchor coupled to a tension element through the myocardium to an operating position adjacent an outer surface of the heart;
  manipulating the anchor to an abutment configuration relative to the outer surface of the heart;
  after inserting the anchor, advancing an electrode having a pole for stimulating the myocardium over the tension element towards the anchor; and
  affixing the tension element to the electrode at a connection point to prevent movement of the electrode in a direction away from the anchor.

* * * * *